United States Patent [19]
Lemon et al.

[11] Patent Number: 5,234,009
[45] Date of Patent: Aug. 10, 1993

[54] TOOTHPICK

[75] Inventors: J. Robert Lemon, Charlotte; William T. Evans, Batesville; Robert E. Christian, Batesville; John Peterson, Batesville; Jane Jones, Greers Ferry, all of Ark.

[73] Assignee: Professional Dental Technologies, Inc., Batesville, Ark.

[21] Appl. No.: 898,213

[22] Filed: Jun. 12, 1992

[51] Int. Cl.$^5$ ............................................. A61C 15/00
[52] U.S. Cl. ...................................... 132/329; 132/321
[58] Field of Search ................................. 132/321, 329

[56] References Cited

U.S. PATENT DOCUMENTS

| | | | |
|---|---|---|---|
| 1,527,028 | 2/1925 | Daniel | 132/321 |
| 2,008,206 | 7/1935 | Grant | 132/329 |
| 3,101,172 | 8/1963 | Wiseman | 132/329 |
| 3,910,293 | 10/1975 | Lemelson | 132/329 |
| 4,135,528 | 1/1979 | Stark | 132/329 |
| 4,271,854 | 6/1981 | Bengtsson | 132/329 |
| 4,314,574 | 2/1982 | Inerte | 132/329 |
| 4,403,625 | 9/1983 | Sanders et al. | |
| 4,570,653 | 2/1986 | Wolf | 132/329 |
| 4,577,649 | 3/1986 | Shimenkov | |
| 4,616,667 | 10/1986 | Tang | |
| 4,651,760 | 3/1987 | Reipur | |
| 4,660,583 | 4/1987 | Brown | |
| 4,712,266 | 12/1987 | Yamaki | |
| 4,805,646 | 2/1989 | Shimenkov | |
| 4,832,061 | 5/1989 | Hwang | |
| 4,846,200 | 7/1989 | Wiley | |

FOREIGN PATENT DOCUMENTS

| | | | |
|---|---|---|---|
| 1084872 | 7/1960 | Fed. Rep. of Germany | 132/329 |
| 1101693 | 3/1961 | Fed. Rep. of Germany | 132/329 |
| 3130971 | 2/1983 | Fed. Rep. of Germany | 132/321 |
| 014334 | 9/1911 | France | 132/329 |
| 0981264 | 5/1951 | France | 132/329 |
| 1509065 | 9/1989 | U.S.S.R. | 132/321 |

Primary Examiner—Gene Mancene
Assistant Examiner—Frank A. LaViola
Attorney, Agent, or Firm—McAulay Fisher Nissen Goldberg & Kiel

[57] ABSTRACT

A toothpick has an elongated body portion having an upwardly extending ridge and a pair of angulated legs defining a longitudinal groove, a tooth gap traversing tip which is substantially flat relatively long and tapers to a point for substantially traversing the gap between adjacent teeth, and a tooth scraping tip which is substantially flat relatively short and tapers to a point for scraping adjacent tooth surfaces in an upward movement. The tips are substantially flexible perpendicular to the flat surfaces for adjusting to the curved surfaces which are encountered in the spaced between teeth. The tips are highly effective in removing food debris from the gap between tooth surfaces yet can be produced at relatively low cost from plastic.

7 Claims, 1 Drawing Sheet

TOOTHPICK

TECHNICAL FIELD

This invention relates generally to implements for cleaning spaces between teeth and more particularly to toothpicks having opposite ends adapted to clean the interstitial spaces and tooth surfaces between adjacent teeth.

BACKGROUND

Conventional toothpicks are typically made of wood, and are either flat having a single point or round having identical opposite round ends ending in a point. These toothpicks are used to remove particles of food from between teeth by thrusting into the spaces into the teeth or by working the food outwardly and away from the gap between the teeth. However, these toothpicks are typically of poor design for matching the openings between the teeth as these may vary significantly from person to person. In some instances, the teeth may be so close together that it is difficult to utilize the toothpick effectively. In addition, wooden toothpicks suffer from rapid delamination and do not maintain sufficient strength to be used effectively.

In U.S. Pat. No. 4,651,760, a toothpick made from plastic is disclosed which has a pointed end supported by a mid portion having longitudinal notches which allows the toothpick to be compressed in a transverse direction and also has transverse flaps which may strike the tooth surfaces. A projecting plate is used as a handle. The flaps also insure that the toothpick attains considerable rigidity to keep its shape even though it may be subject to twisting.

In U.S. Pat. No. 4,805,646, a toothpick is disclosed which has a tapered triangular point which extends from a flexing joint which allows the point to assume various different angles. However, the tip itself is fairly rigid.

U.S. Pat. No. 4,616,667, discloses another toothpick design which has two ends which are pointed, having a shaft, a preferably substantially rectangular transverse cross-section and a longitudinally grooved cleaning tip which permits deformation of the tip in such a manner and direction to reach in between the narrow gaps of teeth while not sacrificing the longitudinal rigidity of the cleaning tip. Consequently, the area adjacent the tip may be bent but the tip itself remains rigid.

While usable, the search continues for toothpicks which are economic to produce yet are readily adaptable to cleaning even narrow, tortuous gaps between teeth.

SUMMARY OF THE INVENTION

It is an object of the present invention to provide a toothpick having dual points which are particularly shaped to conduct different cleaning operations.

It is yet another object of the present invention to provide a toothpick which has a high flexibility, relatively long tapered end to promote planar stiffness but to provide substantial side flexibility for contouring to the space between the teeth.

It is a yet another object to provide a toothpick having a second end with radivsed point having planar stiffness and side flexibility for removing large particles from between teeth.

These and other objects of the present invention are achieved by providing a toothpick having an elongated body with a first end portion, a second end portion opposite the first end portion, and a mid portion having a longitudinal groove therein. The first end portion is substantially flat and has a point obtained by a tapered angle of from about 1° to 5°. The toothpick is composed of a plastic material to provide planar rigidity but permits side bending for contouring to the curved spaces between the teeth. The second end portion is substantially flat and has a point obtained by a tapered angled of about 6° to 10°. The groove in the mid portion permits enhanced gripping of the toothpick. The first end remains substantially flexible to promote full extension of the long tip through the interstitial spaces between adjacent teeth for removal of debris by pushing the tip entirely through the space. The second end is used for removing material by sliding the point along the narrow spacing between the teeth in an upward direction. This point is usable in working out particles trapped between the upper tooth surfaces.

Utilizing the toothpick of the present invention promotes increased effectiveness in removing trapped particles between teeth.

BRIEF DESCRIPTIONS OF THE DRAWINGS

DETAILED DESCRIPTION OF THE INVENTION

Figure 1:
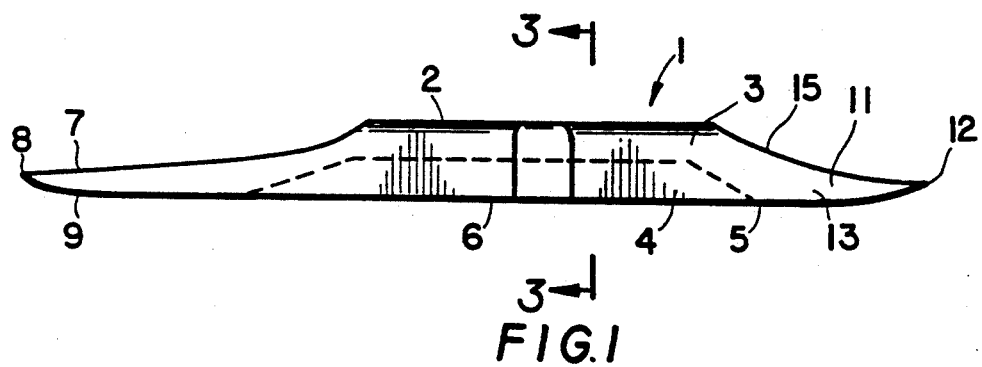
FIG. 1 is a side view of the toothpick of the present invention.
Figure 2:
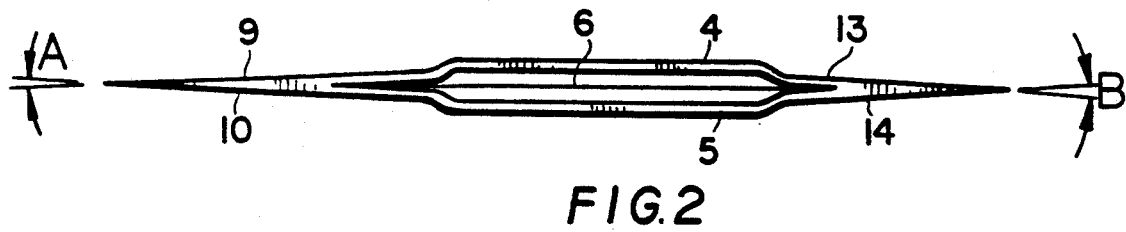
FIG. 2 is a bottom view of the toothpick of FIG. 1.
Figure 3:
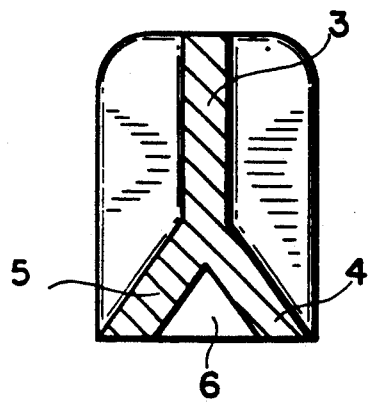
FIG. 3 is a cross-sectional view taken along line 3—3 of FIG. 1.

Referring to FIGS. 1 and 2, a toothpick of the present invention is shown. The toothpick 1 has an elongated body portion 2 made up of an upwardly extending ridge 3 and a pair of downwardly angularly projecting legs 4 and 5. The legs 4 and 5 define a longitudinal gap 6 therebetween.

The toothpick has a tooth gap traversing end 7 which is substantially flat, and of sufficient length to completely traverse a typical tooth gap. A point 8 is formed by tapering the flat side surfaces 9 and 10 at an angle A of about 1° to 7° such that the point is thin and narrow. The thinness of the end assists the point tip in entering and substantially traversing the gap between adjacent teeth. The tip is flexible perpendicular to the flat surfaces which allows the tip to flex around the curved tooth surfaces encountered in the gap between the rear teeth. It is possible to bend the tip to an angle suitable for entering the tooth gap at a right angle to the body portion. However, the end is substantially rigid in the plane of the flat surfaces to prevent collapse and allow some upward movement when necessary. This is a advantage over the other toothpicks since their tips are generally too stiff to be bent at optimum angles for effective tooth cleaning.

The toothpick also has a tooth scraping end 11 which is also substantially flat but relatively short. A point 12 is formed by tapering the flat side surfaces 13 and 14 at an angle B of from about 7° to 14°. The tip is thus thin at the point but relatively thicker as compared to the point 8 such that it only partially enters the gap between adjacent teeth. The end 11 has a curvature at a radius of about 1.0° along an upper edge 15. This point is used for scraping the adjacent tooth surfaces when the point is moved in an upward direction, after the point is partially inserted into the gap. The end 11 is also flexible perpendicular to the flat surfaces to allow bending to enter the gap between the rear teeth. The end is substantially rigid in the plane of the flat surfaces to prevent collapse during the upward translation to dislodge particles.

The toothpick is preferable made of a synthetic resinous polymeric material such as polystyrene, ULTEM ™, polyurethane, nylon or another plastic material. Preferably, the toothpick is made of polystyrene and is produced by injection molding. To accommodate resin flow due to the small size of the toothpick, an enlarged area 16 is provided approximately in the middle of the body portion 2. To promote full resin flow to the points 8 and 12. This is at least as wide as the resin injection port and, when formed, is fairly rigid. However, such an area is not required to practice the invention.

The size of the toothpick is typically about 2 inches in over all length, with the thickness of the ridge and legs being about 0.025 inches. Preferably the elongated tip is about 0.8 inches long. The longitudinal gap, at its widest portion adjacent the ends of the legs may be about 0.070 inches long.

In a preferred embodiment of the invention, the gap traversing tip is tapered at an angle of about 5° and the tooth scraping tip is tapered at an angle of about 8°. Optionally, the tips may have an upward radius along a lower edge thereof to give an upward curvature to the points and minimize the potential for piercing the gum during insertion. Both points may have a lower edge radius at about 0.25° to 0.50°. Due to the elongated nature of the gap traversing point, a radius of about 0.25 is preferred while the tooth scraping tip preferably has a radius at about 0.05°.

While preferred embodiments of the present invention have been shown and described, it will be understood by those skilled in the art that various changes or modifications could be made without varying from the scope of the present invention.

We claim:

1. A toothpick comprising:
   an elongated body portion having an upwardly extending ridge and a pair of angled legs defining a longitudinal groove,
   a tooth gap traversing tip, extending from an end of the elongated body and being substantially flat and of a length sufficient to transverse entirely a gap between adjacent teeth, the end tapering to a flat point, the taper being at an angle of about 1° to 7°, the tip having side flexibility and being substantially rigid in the plane thereof,
   a tooth scraping tip, disposed on the other end of the elongated body, and being substantially flat, and of a length sufficient to partially enter a gap between adjacent teeth, the tip tapering to a flat point at an angle of about 7° to 11°, the tip only partially entering the gap between adjacent teeth for scraping the adjacent tooth surfaces when the toothpick is moved in, an upward direction, the tip having side flexibility and being substantially rigid in the plane thereof.

2. The toothpick of claim 1 wherein the toothpick is composed of a plastic material from the group consisting of polystyrene, polyurethane, ULTEM ™, and nylon.

3. The toothpick of claim 1 wherein the gap traversing tip has a lower edge radius at an angle of about 0.25° to 0.05°.

4. The toothpick of claim 1 wherein the tooth scraping tip has a lower edge radius at an angle of 0.25° to 0.05°.

5. The toothpick of claim 1 wherein the toothpick has an overall length of about 2 inches.

6. The toothpick of claim 1 wherein the tooth gap traversing tip has a taper at an angle of about 5°.

7. The toothpick of claim 1 wherein the tooth scraping tip has a taper at an angle of about 8°.

* * * * *